United States Patent
Ishitani et al.

(10) Patent No.: US 10,781,187 B2
(45) Date of Patent: Sep. 22, 2020

(54) BENZOTRIAZOLE DERIVATIVE COMPOUND

(71) Applicant: SHIPRO KASEI KAISHA, LTD., Sakai, Fukui (JP)

(72) Inventors: Tomoyuki Ishitani, Sakai (JP); Toshiyuki Uesaka, Sakai (JP); Takuya Iwamoto, Sakai (JP)

(73) Assignee: SHIPRO KASEI KAISHI, LTD., Sakai (JP)

( * ) Notice: Subject to any disclaimer, the term of this patent is extended or adjusted under 35 U.S.C. 154(b) by 0 days.

(21) Appl. No.: 16/604,694

(22) PCT Filed: Apr. 6, 2018

(86) PCT No.: PCT/JP2018/014816
§ 371 (c)(1),
(2) Date: Oct. 11, 2019

(87) PCT Pub. No.: WO2018/190281
PCT Pub. Date: Oct. 18, 2018

(65) Prior Publication Data
US 2020/0157059 A1    May 21, 2020

(30) Foreign Application Priority Data
Apr. 13, 2017   (JP) ................. 2017-079707

(51) Int. Cl.
*C07D 249/20*   (2006.01)
*C08K 5/3475*   (2006.01)
*C08L 101/00*   (2006.01)

(52) U.S. Cl.
CPC .......... *C07D 249/20* (2013.01); *C08K 5/3475* (2013.01); *C08L 101/00* (2013.01)

(58) Field of Classification Search
CPC .... C07D 249/20; C08K 5/3475; C08L 101/00
See application file for complete search history.

(56) References Cited

U.S. PATENT DOCUMENTS

| 3,738,837 A | 6/1973 | Kuwabara et al. |
| 2010/0103352 A1 | 4/2010 | Suzuki et al. |

FOREIGN PATENT DOCUMENTS

| JP | 2004-307376 A | 11/2004 |
| JP | 2007-297469 A | 11/2007 |
| JP | 2012-25680 A | 2/2012 |
| WO | WO 2008/126700 A1 | 10/2008 |

OTHER PUBLICATIONS

International Search Report for PCT/JP2018/014816 dated May 29, 2018.
Written Opinion of the International Searching Authority for PCT/JP2018/014816 (PCT/ISA/237) dated May 29, 2018.

*Primary Examiner* — Joseph R Kosack
(74) *Attorney, Agent, or Firm* — Birch, Stewart, Kolasch & Birch, LLP

(57) ABSTRACT

Provided are benzotriazole derivative compounds of the general formula that are novel compounds capable of strongly absorbing light in the ultraviolet range, particularly 300-330 nm, while strongly absorbing light in the visible light short-wavelength range up to around 450 nm and being used suitably as a light absorber having high light fastness with a light-blocking function over an extended period of time. [Preferably, $R_1$ is a hydrogen atom or alkyl group, $R_2$ is a C1-8 alkyl group, $R_3$ is a hydrogen atom, alkyl group, acryloyloxyalkyl group, or methacryloyloxyalkyl group].

3 Claims, 6 Drawing Sheets

BENZOTRIAZOLE DERIVATIVE COMPOUND

TECHNICAL FIELD

The present invention relates to a new benzotriazole derivative compound. The present invention also relates to a light absorber and a resin composition that includes the new benzotriazole. In more detail the present invention relates to a light absorber and a resin composition capable of strongly absorbing an ultraviolet light and a visible light short wavelength range by exhibiting a maximum absorption wavelength in a vicinity of 310 nm and 380 nm.

BACKGROUND ART

It is well known that organic materials such as a resin and the like degrade by a function of ultraviolet light of solar light. In the resin, coloration or decrease in strength occurs by the ultraviolet light, and in a variety of functional organic materials, decomposition is caused by the ultraviolet light and their functions degrade.

In order to prevent the degradation of these organic materials caused by the ultraviolet light, an ultraviolet light absorber is generally used. For example, in a display device, it is generally practiced to add the ultraviolet light absorber to optical films such as polarizer protective films and the like thereby preventing the coloration of these optical films. Also, in order to prevent the degradation of a near-infrared light absorber included in anti-reflection films caused by the ultraviolet light, the ultraviolet light absorber is added to the anti-reflection films. Further, a variety of organic materials such as fluorescent elements, phosphorescent elements, and the like are used in a luminous element of organic EL displays. That is to say, in order to prevent the degradation of the organic materials caused by the ultraviolet light, the ultraviolet absorber is added to a surface film of the display.

In human bodies, it is well known that skins and eyeballs get tanned by the ultraviolet light, causing various maladies. The bad effect to the eyeballs caused by the ultraviolet light includes, for example, a possible development of a cornea inflammation when the eyes are exposed to solar light in such an outdoor place where there are lots of ultraviolet light. As for the bad effect to lens, a cataract might be developed by the accumulated ultraviolet light.

In order to prevent various diseases related to eyeballs caused by the ultraviolet light, it is generally practiced to add the ultraviolet absorber to glass lens or contact lens, thereby preventing the ultraviolet light from reaching the eyes.

Further, recently, it has been pointed out that among solar lights, not only the ultraviolet light of not greater than 400 nm but also the light of visible light short wavelength range of around 400 to 450 nm may badly affect human bodies, and for the specific uses including the above mentioned use, such a light absorber is required that can absorb the light of visible light long wavelength range.

For each of the above mentioned uses, some light absorbers have been proposed that efficiently absorb the ultraviolet light and the light of visible light short wavelength range, and as compounds that have an absorbing function in such a wavelength range, for example, as described in Patent Documents 1 to 2, indole derivative, pyrrolidine-amide derivative, and xanthon derivative are exemplified. However, in general, these compounds have low light resistance property and therefore, they degrade by being exposed to solar light and have low light absorbing capability. Thus, they cannot be used for a long period of time. Further, Patent Documents 1 to 2 have no descriptions on light resistance property.

Patent documents 3 to 4 propose a light absorber capable of efficiently absorbing the ultraviolet light and the light of the short wavelength range, by modifying benzotriazole with sesamol that is generally known to have high light resistance. However, such a light absorber is weak in absorbing the light of not less than 420 nm although it does absorb the visible light short wavelength range. It also has a weakness in its capability of absorbing ultraviolet light range in the vicinity of 300 to 330 nm.

PRIOR ART DOCUMENTS

Patent Documents

Patent document 1: Official Gazette, Patent Publication No2012-58643
Patent document 2: Official Gazette, Patent Publication No2007-284516
Patent Document 3: Official Gazette, Patent Publication No2012-41333
Patent Document 4: Official Gazette, Patent Publication No2012-25680

SUMMARY OF THE INVENTION

Problem to be Solved by the Invention

In view of the above situations, the object of the present invention is to provide a new compound capable of preferably being used as a light absorber that absorbs strongly the ultraviolet light range in particular of 300 to 330 nm to show a high light resistance having a light blocking function in a long term range, while strongly absorbing ultraviolet the light of visible light short wavelength range to the vicinity of 450 nm.

Means to Solve the Problem

In the present invention, the main means to solve the above mentioned problem is providing a new benzotriazole derivative compound as represented by the following general formula (1).

[Chemical 1]

General formula (1)

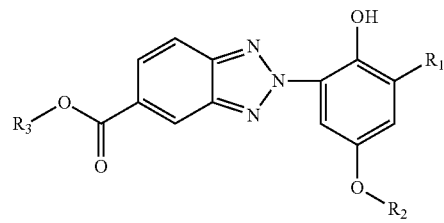

[in the general formula (1), $R_1$ represents a hydrogen atom or an alkyl group whose carbon number is 1 to 8, $R_2$ represents a hydrogen atom, an alkyl group whose carbon number is 1 to 18, a carboxyalkyl group whose alkyl carbon number is 1 to 7, an alkyl oxycarbonylalkyl group of which a total alkyl carbon number is 2 to 15, an acryloyl oxyalkyl group whose alkyl carbon number is 1 to 4, an acryloyl oxyhydroxyalkyl group whose alkyl carbon number is 1 to 4, a methacryloyl oxyalkyl group whose alkyl carbon number is 1 to 4, or a methacryloyl oxyhydroxyalkyl group whose alkyl carbon number is 1 to 4, $R_3$ represents a hydrogen atom or an alkyl group whose carbon number is 1 to 18, a carboxyalkyl group whose alkyl carbon number is 1 to 7, an alkyloxycarbonylalkyl group of which a total alkyl carbon number is 2 to 15, a hydroxyalkyl group whose carbon number is 1 to 8, an alkylcarbonylalkyl group of which a total alkyl carbon number is 2 to 15, phenyl group, tolyl group, an acryloyl oxyalkyl group whose alkyl carbon number is 1 to 4, an acryloyl oxyhydroxyalkyl group whose alkyl carbon number is 1 to 4, a methacryloyl oxyalkyl group whose alkyl carbon number is 1 to 4, or a methacryloyl oxyhydroxyalkyl group whose alkyl carbon number is 1 to 4.]

In benzotriazole compound represented by the above general formula (1), it is preferable that $R_1$ represents a hydrogen atom or an alkyl group whose carbon number is 1 to 8, that $R_2$ is an alkyl group whose carbon number is 1 to 8, and that $R_3$ represents a hydrogen atom or an alkyl group whose carbon number is 1 to 8, or an acryloyloxyalkyl group whose alkyl carbon number is 1 to 2 or a methacryloyloxyalkyl group whose alkyl carbon number is 1 to 2.

Effect of the Invention

Benzotriazole derivative compound represented by general formula (1) of the present invention has a carboxyl group in the 5th position of a benzotriazole ring and also has a hydroxy group or an alcoxy group in the para position of a phenolic ring, and therefore, it shows a maximum absorbing wavelength in the vicinity of 310 nm and 380 nm to strongly absorb the ultraviolet light and the visible light short wavelength range, and has a high light-resistance that shows the light blocking function in a long term. Therefore, the benzotriazole derivative compound of the present invention is useful as a light absorber capable of solving the problem that the prior art used to have.

Best Embodiment for Carrying Out the Invention

Hereinafter, the detailed explanations are given for the present invention. In the present invention, as an ultraviolet light absorber and as a resin composition, benzotriazole derivative compound represented by general formula (1) is used. Hereinafter, the explanations are given for the compound represented by general formula (1).

[Chemical 1]

General formula (1)

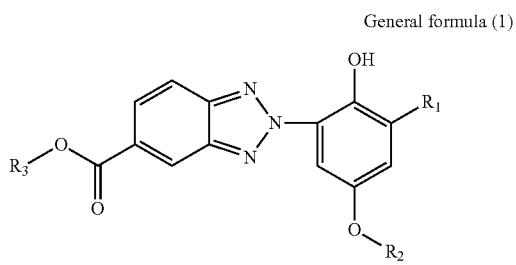

In general formula (1), $R_1$ exemplifies a hydrogen atom or a linear or branched alkyl group, etc whose carbon number is 1 to 8 such as methyl group, ethyl group, propyl group, isopropyl group, butyl group, isobutyl group, sec-butyl group, tert-butyl group, hexyl group, octyl group, 2-ethylhexyl group, etc, $R_2$ exemplifies a hydrogen atom or a linear or branched alkyl group, etc whose carbon number is 1 to 18 such as methyl group, ethyl group, propyl group, isopropyl group, butyl group, isobutyl group, sec-butyl group, tert-butyl group, hexyl group, octyl group, 2-ethylhexyl group, dodecyl group, octadecyl group, etc; carboxyalkyl group whose alkyl carbon number is 1 to 7, such as carboxyethyl group, carboxyheptyl group, etc; an alkyl oxycarbonylalkyl group of which a total of each alkyl carbon number is 2 to 15 such as methoxycarbonyl ethyl group, octyloxycarbonyl heptyl group, etc; a hydroxyalkyl group whose carbon number is 1 to 8, such as hydroxyethyl group, hydroxyoctyl group, etc; an alkylcarbonyloxyalkyl group of which a total of each alkyl carbon number is 2 to 15, an acryloyloxyalkyl group whose alkyl carbon number is 1 to 4, such as an acryloyloxyethyl group, an acryloyloxybutyl group, etc; a methacryloyloxyalkyl group whose alkyl carbon number is 1 to 4, such as a methacryloyloxyethyl group, a methacryloyloxybutyl group; or a methacryloyloxyhydroxyalkyl group whose alkyl carbon number is 1 to 4, such as methacryloyloxy-2-hydroxypropyl group, etc, and $R_3$ exemplifies a hydrogen atom or a linear or branched alkyl group, etc whose carbon number is 1 to 18 such as methyl group, ethyl group, propyl group, isopropyl group, butyl group, isobutyl group, sec-butyl group, tert-butyl group, hexyl group, octyl group, 2-ethylhexyl group, dodecyl group, octadecyl group, etc; carboxyalkyl group whose alkyl carbon number is 1 to 7, such as carboxyethyl group, carboxyheptyl group, etc; an alkyl oxycarbonylalkyl group of which a total of each alkyl carbon number is 2 to 15 such as methoxycarbonyl ethyl group, octyloxycarbonylheptyl group, etc; a hydroxyalkyl group whose carbon number is 1 to 8, such as hydroxyethyl group, hydroxyoctyl group, etc; an alkylcarbonyloxyalkyl group of which a total of each alkyl carbon number is 2 to 15 such as methoxycarbonyl ethyl group, octyloxycarbonylheptyl group, etc; a hydroxyalkyl group whose carbon number is 1 to 8, such as hydroxyethyl group, hydroxyoctyl group, etc; an alkylcarbonyloxyalkyl group of which a total of each alkyl carbon number is 2 to 15 such as a methylcarbonyloxyethyl group, a heptylcarbonyloxyoctyl group, etc; a phenyl group, a tolyl group, an acryloyloxyalkyl group whose alkyl carbon number is 1 to 4, such as an acryloyloxyethyl group, an acryloyloxybutyl group, etc; an acryloyloxyhydroxy group whose alkyl carbon number is 1 to 4, such as acroyloxy-2-hydroxypropyl group, etc; a methacryloyloxyalkyl group whose alkyl carbon number is 1 to 4, such as a methacryloyloxybutyl group, etc; or a a methacryloyloxyalkyl group whose alkyl carbon number is 1 to 4, such as a methacroyloxy-2-hydroxypropyl group, etc.

In benzotriazole compound represented by the above general formula (1), it is preferable that $R_1$ represents a hydrogen atom or an alkyl group whose carbon number is 1 to 8, that $R_2$ is an alkyl group whose carbon number is 1 to 8, and that $R_3$ represents a hydrogen atom or an alkyl group whose carbon number is 1 to 8, or an acryloyloxyalkyl group whose alkyl carbon number is 1 to 2 or a methacryloyloxyalkyl group whose alkyl carbon number is 1 to 2.

As general formula (1) of the benzotriazole derivative compound of the present invention, the following can be exemplified. Methyl 2-(2-hydroxy-5-methoxyphenyl)-2H-benzotriazole-5-carboxylate, methyl 2-(3-tert-butyl-2-hydroxy-5-methoxyphenyl)-2H-benzotriazole-5-carboxylate, methyl 2-(2-hydroxy-5-methoxy-3-tert-octylphenyl)-2H-benzotriazole-5-carboxylate, octyl 2-(3-tert-butyl-2-hydroxy-5-methoxyphenyl)-2H-benzotriazole-5-carboxylate, 2-ethylhexyl 2-(3-tert-butyl-2-hydroxy-5-methoxyphenyl)-2H-benzotriazole-5-carboxylate, octyl 2-(3-tert-butyl-2-hydroxy-5-methoxyphenyl)-2H-benzotriazole-5-carboxylate, methyl 2-[3-tert-butyl-2-hydroxy-5-(2-methacryloyloxyethoxy) phenyl]-2H-benzotriazole-5-carboxylate, phenyl 2-(3-tert-butyl-2-hydroxy-5-methoxyphenyl)-2H-benzotriazole-5-carboxylate, 2-methacryloyloxyethyl 2-(2-hydroxy-5-methoxyphenyl)-2H-benzotriazole-5-carboxylate, 2-acryloyloxyethyl 2-(3-tert-butyl-2-hydroxy-5-methoxyphenyl)-2H-benzotriazole-5-carboxylate, 2-methacryloyloxyethyl 2-(3-tert-butyl-2-hydroxy-5-methoxyphenyl)-2H-benzotriazole-5-carboxylate.

Although a method of synthesizing general formula (1) of the benzotriazole derivative compound of the present invention is not specifically limited and a publicly known reaction principle an widely be used, it can be synthesized through the reaction formula shown in the following (chemicals 2 to 7), for example.

[Chemical 2]

[Chemical 3]

[Chemical 4]

[Chemical 5]

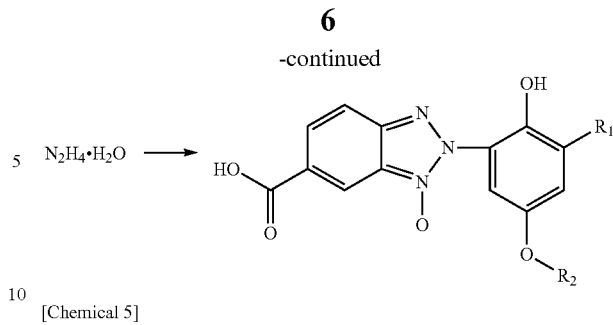

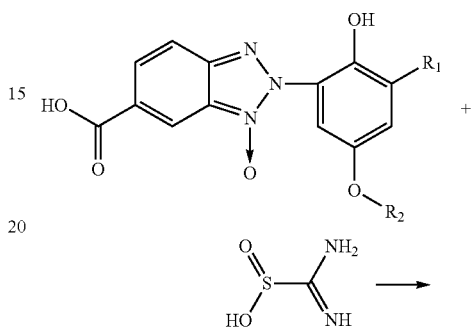

[Chemical 6]

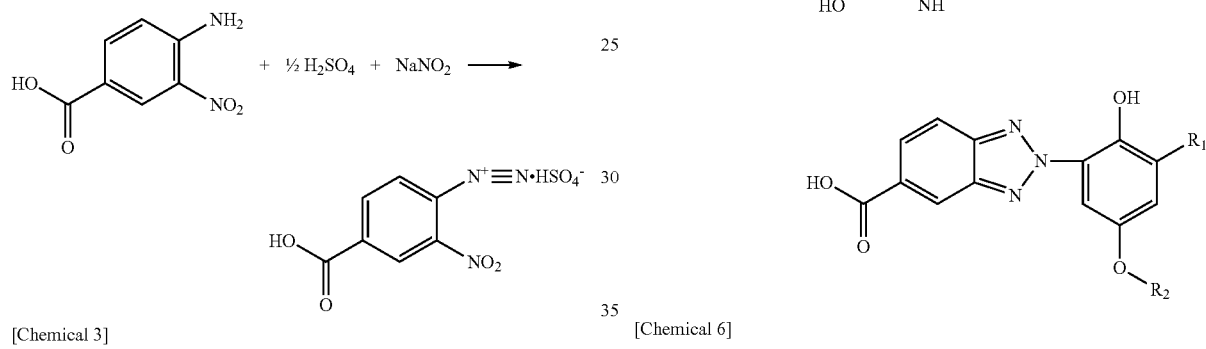

[Chemical 7]

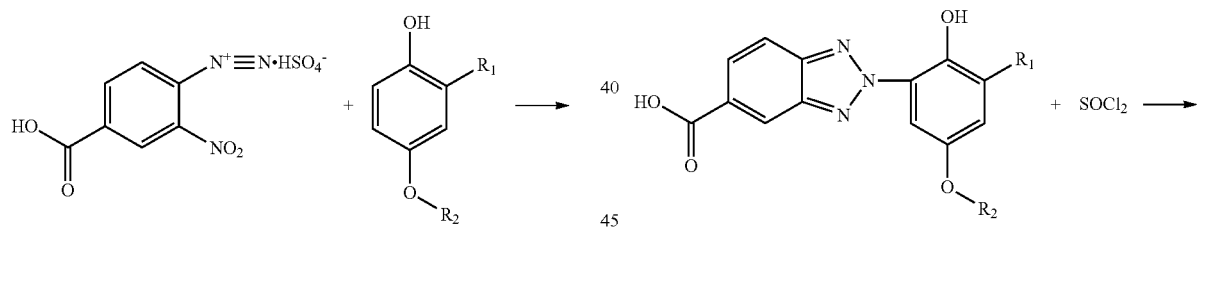

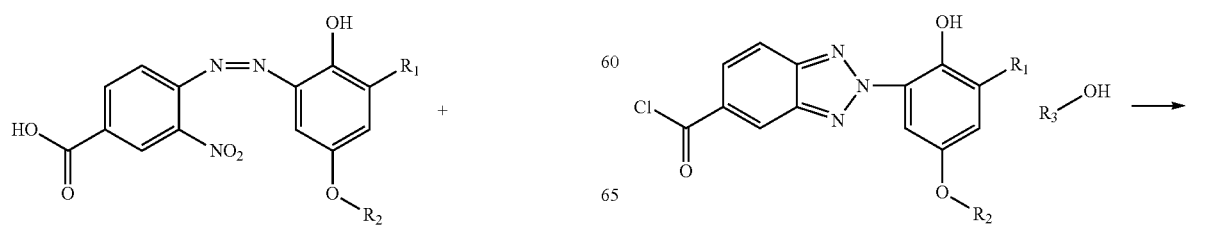

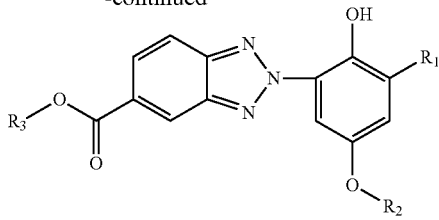

In the benzotriazole derivative compounds of the present invention, regarding those having a polymerizable double bond, homopolymerization or copolymerization are possible. Although other copolymerizable polymers are not specifically limited, for example, acrylic ester such as methyl acrylate, ethyl acrylate, propyl acrylate, butyl acrylate, hexyl acrylate, octyl acrylate, or methacrylic ester such as methyl methacrylate, ethyl methacrylate, propyl methacrylate, butyl methacrylate, hexyl methacrylate, octyl methacrylate, can be exemplified.

Although the resin to which the benzotriazole derivative compound of the present invention may be added is not specifically limited, α olefin polymer or ethylene-vinyl acetate copolymer such as polyethylene, polypropylene, polybutene, polypentene, poly-3-methyl butylene, and polymethyl pentene, polyolefin such as ethylene-propylene copolymer, polyvinyl chloride, polyvinyl bromide, polyvinyl fluoride, chlorinated polyethylene, chlorinated polypropylene, brominated polyethylene, chlorinated rubber, vinyl chloride-vinyl acetate copolymer, vinyl chloride-ethylene copolymer, vinyl chloride-propylene copolymer, vinyl chloride-styrene copolymer, vinyl chloride-isobutylene copolymer, vinyl chloride-vinylidene copolymer, vinyl chloride-styrene-maleic anhydride ternary copolymer, vinyl chloride-styrene-acrylonitrile ternary copolymer, vinyl chloride-butadiene copolymer, vinyl chloride-isobutylene copolymer, vinyl chloride-chlorinated propylene copolymer, vinyl chloride-vinylidene chloride-vinyl acetate ternary copolymer, vinyl chloride-acrylic ester copolymer, vinyl chloride-maleic ester copolymer, vinyl chloride-methacrylate ester copolymer, vinyl chloride-acrylonitrile copolymer, halogen containing synthetic resin such as internal plasticity polyvinyl chloride, petroleum resin, coumarone resin, polystyrene, copolymer of styrene and other monomer (such as maleic anhydride, butadiene, acrylonitrile), styrene resin such as acrylonitrile-butadiene-styrene resin, acrylic ester-butadiene-styrene resin, and methacrylic ester-butadiene-styrene resin, polyvinyl acetate, polyvinyl alcohol, polyvinyl formal, polyvinyl butyral, acrylic resin, methacrylic resin, polyacrylonitrile, polyphenylene oxide, polycarbonate, denaturalized polyphenylene oxide, polyacetal, phenolic resin, urea resin, melamine resin, epoxy resin, silicone resin, polyethylene terephthalate, reinforced polyethylene terephthalate, polybutyrene terephthalate, polysulfone resin, polyether sulfone, polyphenylene sulfide, polyether ketone, polyether imide, polyixy benzoile, polyimide, polymareimide, polyamide imide, alkyd resin, amino resin, vinyl resin, er soluble resin, powder paint resin, polyamide resin, polyurethane resin, polythiourethane resin, unsaturated polyester resin can be exemplified.

In adding the benzotriazole derivative compound of the present invention to a resin, as an ultraviolet light absorber, only the benzotriazole derivative compound of the present invention can be used or it can be used in combinations with other ultraviolet light absorbers. Regarding ultraviolet light absorbers other than the benzotriazole derivative compound of the present invention, they are not specifically limited and they can be used as far as they can be obtained in general markets and as far as they can absorb the ultraviolet region. For example, benzotriazole derivatives, benzophenone derivatives, salicylate derivatives, cyanoacrylate derivatives, triazine derivatives and the like are used. The ultraviolet light absorber can be used alone or two or more of them can be mixed together, as appropriate.

The benzotriazole derivative compound of the present invention can be used by 0.01 to 10 wt % with respect to the resin, and preferably by 0.1 to 1 wt % with respect to the resin.

EXAMPLES

Hereinafter, a method of synthesizing the benzotriazole derivative compound experimented in the present invention, and properties of the compound are shown. However, the present invention is not limited to these embodiments.

Example 1

Synthesis of compound (a); 2-methacryloyloxyethyl 2-(3-tert-butyl-2-hydroxy-5-methoxyphenyl)-2H-benzotriazole-5-carboxylate

[Chemical 8]

Compound (a)

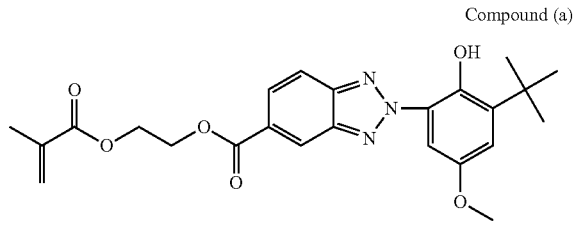

To a four-neck flask of 200 ml, a balled condenser, a thermometer, and a mixing device were attached, in which 100 ml of water, 6.5 g (0.061 mol) of sodium carbonate, 20.0 g (0.110 mol) of 4-amino-3-nitro benzoic acid were put and dissolved, to which 22.7 g (0.118 mol) of an aqueous solution of 36% sodium nitrite were added. To a four-neck flask of 500 ml, a balled condenser, a thermometer, and a mixing device were attached, in which 100 ml of water and 43.0 g (0.274 mol) of 62.5% sulfuric acid and cooled to 3 to 7° C., onto which the mentioned solution was dripped, followed by mixing it at the same temperature for 2 hours to obtain an aqueous solution of diazonium salt. To a four-neck flask of 1000 ml, a balled condenser, a thermometer, and a mixing device were attached, in which 18.0 g (0.100 mol) of 2-tert-butyl-4-methoxyphenol, 10 ml of isopropyl alcohol, and 140 ml of water were put and mixed, onto which an aqueous solution of diazonium salt was dripped at 5 to 10° C. for 2 hours, further followed by mixing for 12 hours at 10 to 15° C. to obtain a slurry liquid of 2-tert-butyl-6-(4-carboxy-2-nitrophenylazo)-4-methoxyphenol. 27.8 g (0.222 mol) of an aqueous solution of 32% sodium hydroxide and 200 ml of isopropyl alcohol were added thereto, followed by removing a water layer in a bottom layer at 70° C. 30.0 g (0.222 mol) of an aqueous solution of 32% sodium hydroxide, 200 ml of water, and 0.4 g of hydroquinone were added thereto, followed by dripping 6.0 g (0.072 mol) of 60% hydraxine-hydrate at 40 to 50° C. for 1 hour, followed by mixing at the same temperature for 2 hours. Then the pH value was adjusted to 4 by 62.5% sulfuric acid, followed by filtering, rinsing, and drying the generated sediment to obtain 23.6 g of 5-carboxy-2-(3-tert-butyl-2-hydroxy-5-methoxyphenyl)-2H-benzotriazole N-oxide.

To a four-neck flask of 500 ml, a balled condenser, a thermometer, and a mixing device were attached, in which 23.6 g (0.066 mol) of 5-carboxy-2-(3-tert-butyl-2-hydroxy-5-5methoxyphenyl)-2H-benzotriazole N oxide, 100 ml of isopropyl alcohol, 100 ml of water, and 24.0 g (0.192 mol) of an aqueous solution of 32% sodium hydroxide were put, to which 12.0 g (0.111 mol) of a thiourea dioxide was added at 70 to 80° C. taking for 3 hours. It was mixed at the same temperature for 1 hour, followed by removing the water layer in the bottom layer by separating it, followed by adjusting the pH value to 4 by using 62.5% sulfuric acid, further followed by filtering, rinsing, and drying the generated sediment, thereby obtaining 20.3 g of 5-carboxy-2-(3-tert-butyl-2-hydroxy-5-5methoxyphenyl)-2H-benzotriazole.

To a four-neck flask of 300 ml, a balled condenser, a thermometer, and a mixing device were attached, to which 20.3 g (0.059 mol) of 5-carboxy-2-(3-tert-butyl-2-hydroxy-5-5methoxyphenyl)-2H-benzotriazole, 100 ml of toluene, 13.0 g (0.109 mol) of thionyl chloride, and 2.0 ml of N,N-dimethylformamide were put and were mixed at 60 to 70° C. for 3 hours. Subsequently, by depression, the solvent was recovered, followed by adding 100 ml of toluene, 14.0 g (0.108 mol) of methacrylic acid 2-hydroxyethyl, and 8.3 g (0.105 mol) of pyridine, and were mixed at 60 to 70° C. for 1 hour. 20 ml of water and 9.0 g (0.057 mol) of 62.5% sulfuric acid were added thereto and the water layer of the bottom layer were separated at 60 to 70° C. and removed, followed by recovering the toluene by depression, to which 90 ml of isopropyl alcohol was added, further followed by filtering, rinsing, and drying the generated sediment thereby obtaining a coarse crystal. This coarse crystal was recrystalized to obtain 22.2 g of compound (a). The yield was 49% (from 2-tert-butyl-4-methoxyphenol). A melting point was 124° C.

In the meantime, by HPLC analysis, a purity of the compound (a) was measured.
<Condition of Measurement>
  Apparatus: L-2130 (Hitachi High-Technologies Corporation)
  Column used: SUMIPAX ODS A-212 6.0×150 mm 5 μm
  Column temperature: 40° C.
  Mobile phase: methanol/water=95/5 (3 ml phosphoric acid/L)
  Flow velocity: 1.0 ml/min
  Detection: UV250 nm
<Result of Measurement>
  HPLC surface purity: 98.5%

For information, the HPLC measurement was conducted under the same measurement condition as above in the following Examples 2 to 5.

The ultraviolet-visible absorption spectrum of the compound (a) was measured, and it was found that the maximum absorption wavelength λmax was 313.2 nm and 382.8 nm, respectively, and the molar extinction coefficient ε of the wavelength was 14800 and 12700, respectively. The spectrum is shown in FIG. 1. The measurement condition of the spectrum is as follows:
<Condition of Measurement>
  Apparatus: UV-2450 (Shimadzu Corporation)
  Measurement wavelength: 250 to 500 nm
  Solvent: chloroform
  Concentration: 10 ppm For information, the ultraviolet-visible absorption spectrum was measured under the same measurement condition as above in the following Examples 3 to 6.

Further, as the result of the NMR measurement of the compound (a), the above structure was supported. The measurement condition is as follows:
<Condition of Measurement>
  Apparatus: JEOL JNM-AL300
  Resonant frequency: 300 MHz (1H-NMR)
  Solvent: chloroform-d As an internal standard substance of 1H-NMR, tetramethylsilane was used, and the chemical shift value was represented by δ value (ppm) and the coupling constant was represented by Hertz. Further, s represents an abbreviation of singlet, d that of doublet, t that of triplet, and m that of multiplet. The same is applied to the following Examples 2 to 6. For information, in the following Examples 2 to 6, the NMR measurement was conducted as in the present Example. The content of the NMR spectrum obtained is as follows:

δ=11.44 (s, 1H, phenol-OH), 8.73 (m, 1H, benzotriazole-H), 8.13 (d, 1H, J=9.0 Hz, benzotriazole-H), 7.98 (d, 1H, J=11.1 Hz, benzotriazole-H), 7.82 (s, 1H, phenol-H), 7.05 (s, 1H, phenol-H), 6.18 (s, 1H, C=CH$_2$—H), 5.62 (s, 1H, C=CH$_2$—H), 4.65 (m, 2H, methacryloyl-O—CH$_2$—H), 4.56 (m, 2H, benzotriazole-CO—O—CH$_2$—H), 3.93 (s, 3H, phenol-O—CH$_3$—H), 1.98 (s, 3H, CH$_2$=—C—CH$_3$—H), 1.56 (s, 9H, tert-butyl-H)

Example 2

[Synthesis of compound [b]; 2-acryloyloxyethyl 2-(3-tert-butyl-2-hydroxy-5-methoxyphenyl)-2H-benzotriazole-5-carboxylate]

[Chemical 9]

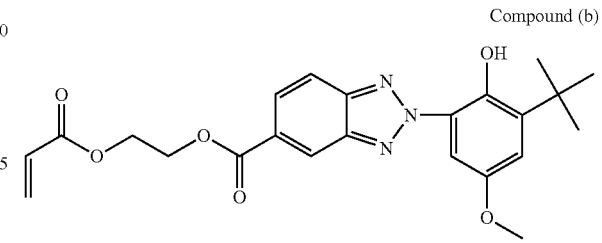

Compound (b)

Compound (b) was obtained with the yield of 46% (from 2-tert-butyl-4-methoxyphenyl) in the same manner as in Example 3 except that acrylate acid 2-hydroxyethyl was used instead of methacrylate acid 2-hydroxyethyl. The melting point was 126° C. and the HPLC surface purity was 98.1%.

Further, when the ultraviolet-visible absorption spectrum of the compound (b) was measured, the maximum absorption wavelength λmax was 313.2 nm and 380.6 nm, respectively, and the molar extinction coefficient E of the wavelength was 15400 and 13100, respectively. The spectrum is shown in FIG. 2. The measurement condition of the spectrum is as follows:
<Condition of Measurement>
  Apparatus: UV-1850 (Shimadzu Corporation)
  Measurement wavelength: 250 to 500 nm
  Solvent: chloroform
  Concentration: 10 ppm Further, as the result of the NMR measurement of the compound (b), the above structure was supported. The measurement condition is as follows:

δ=11.39 (s, 1H, phenol-OH), 8.72 (s, 1H, benzotriazole-H), 8.12 (d, 1H, J=9.0 Hz, benzotriazole-H), 7.96 (d, 1H, J=9.0 Hz, benzotriazole-H), 7.81 (s, 1H, phenol-H), 7.05 (s, 1H, phenol-H), 6.46 (m, 1H, CH=CH$_2$—H), 6.20 (m, 1H, CH$_2$=CH—H), 5.89 (m, 1H, CH=CH$_2$—H), 4.64 (m, 2H, acryloyl-O—CH$_2$—H), 4.57 (m, 2H, acryloyl-O—CH$_2$—C—H$_2$—H), 3.81 (s, 3H, phenol-O—CH$_3$—H), 1.50 (s, 9H, tert-butyl-H)

Example 3

Synthesis of compound (c); methyl 2-(3-tert-butyl-2-hydroxy-5-methoxyphenyl)-2H-benzotriazole-5-carboxylate

[Chemical 10]

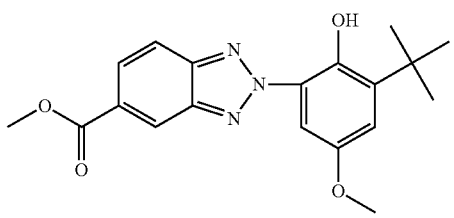

Compound (c)

Compound (c) was obtained with the yield of 53% (from 2-tert-butyl-4-methoxyphenyl) in the same manner as in Example 1 except that methyl alcohol was used instead of methacrylate acid 2-hydroxyethyl. The melting point was 154° C. and the HPLC surface purity was 99.4%. The maximum absorption wavelength A max was 312.6 nm and 381.6 nm, respectively, and the molar extinction coefficient ε of the wavelength was 14800 and 13000, respectively. The spectrum is shown in FIG. 3.

Further, as the result of measuring the NMR of the compound (c), the above structure was supported. The content of the obtained NMR is as follows:

δ=11.40 (s, 1H, phenol-OH), 8.69 (s, 1H, benzotriazole-H), 8.10 m, 1H, benzotriazole-H), 7.96 (m, 1H, benzotriazole-H), 7.80 (s, 1H, phenol-H), 7.04 (s, 1H, phenol-H), 4.04 (s, 3H, benzotriazole-C—O—O—CH$_3$—H), 3.84 (s, 3H, phenol-O—CH$_3$—H), 1.50 (s, 9H, tert-butyl-H)

Example 4

Synthesis of compound (d); octyl 2-(3-tert-butyl-2-hydroxy-5-methoxyphenyl)-2H-benzotriazole-5-carboxylate

[Chemical 11]

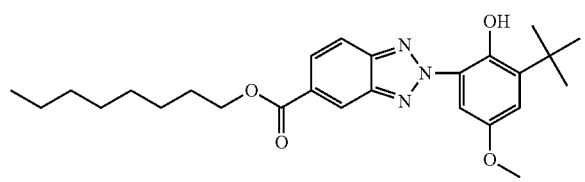

Compound (d)

Compound (d) was obtained with the yield of 32% (from 2-tert-butyl-4-methoxyphenyl) in the same manner as in Example 1 except that octyl alcohol was used instead of methacrylate acid 2-hydroxyethyl. The melting point was 130° C. and the HPLC surface purity was 99.7%. The maximum absorption wavelength A max was 312.8 nm and 379.8 nm, respectively, and the molar extinction coefficient ε of the wavelength was 14600 and 13000, respectively. The spectrum is shown in FIG. 4.

Further, as the result of measuring the NMR of the compound (d), the above structure was supported. The content of the obtained NMR is as follows.

δ=11.44 (s, 1H, phenol-OH), 8.71 (s, 1H, benzotriazole-H), 8.11 (d, 1H, J=1.5 Hz, benzotriazole-H), 7.97 (m, 1H, benzotriazole-H), 7.81 (s, 1H, phenol-H), 7.05 (s, 1H, phenol-H), 4.39 (m, 2H, benzotriazole-C—O—O—CH$_2$—H), 3.90 (s, 3H, phenol-O—CH$_3$—H), 1.50 (m, 21H, octyl-CH$_2$, tert-butyl-H), 0.90 (m, 3H, octyl-CH$_3$)

Example 5

Synthesis of compound (e); 2-ethylhexyl 2-(3-tert-butyl-2-hydroxy-5-methoxyphenyl)-2H-benzotriazole-5-carboxylate

[Chemical 12]

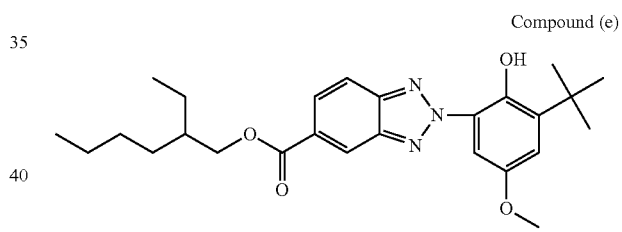

Compound (e)

Compound (e) was obtained with the yield of 37% (from 2-tert-butyl-4-methoxyphenyl) in the same manner as in Example 1 except that 2-ethylhexyl alcohol was used instead of methacrylate acid 2-hydroxyethyl. The melting point was 81° C. and the HPLC surface purity was 99.8%. The maximum absorption wavelength λmax was 312.8 nm and 379.8 nm, respectively, and the molar extinction coefficient ε of the wavelength was 15100 and 13100, respectively. The spectrum is shown in FIG. 5.

Further, as the result of measuring the NMR of the compound (e), the above structure was supported. The content of the obtained NMR is as follows.

δ=11.46 (s, 1H, phenol-OH), 8.73 (s, 1H, benzotriazole-H), 8.13 (d, 1H, J=9.0 Hz, benzotriazole-H), 7.97 (d, 1H, J=9.0 Hz, benzotriazole-H), 7.82 (s, 1H, phenol-H), 7.05 (s, 1H, phenol-H), 4.32 (m, 2H, benzotriazole-C—O—O—CH$_2$—H), 3.90 (s, 3H, phenol-O—CH$_3$—H), 1.50 (m, 18H, tert-butyl-H, 2-ethylhexyl-CH$_2$, 2-ethylhexyl-CH), 0.96 (m, 6H, 2-ethylhexyl-CH$_3$)

Example 6

Synthesis of compound (f); 2-methacyloyl oxyethyl 2-(2-hydroxy-5-methoxyphenyl)-2H-benzotriazole-5-carboxylate

[Chemical 13]

Compound (f)

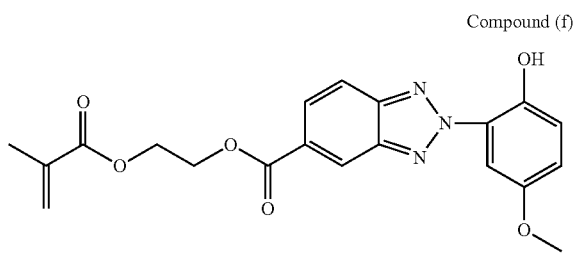

Compound (f) was obtained with the yield of 5% (from 4-methoxyphenyl) in the same manner as in Example 1 except that 4-methoxyphenol was used instead of 2-tert-butyl-4-methoxyphenol. The melting point was 94° C. and the maximum absorption wavelength λ max was 309.8 nm and 373.2 nm, respectively, and the molar extinction coefficient ε of the wavelength was 14700 and 13100, respectively. The spectrum is shown in FIG. 6.

Further, by HPLC analysis, a purity of the compound (e) was measured.

<Condition of Measurement>

Apparatus: L-2130 (Hitachi High-Technologies Corporation)

Column used: Inertsil ODS-3 4.6×150 mm 5 μm

Column temperature: 25° C.

Mobile phase: acetonitrile/water=9/1 (phosphoric acid 3 ml/L)

Flow velocity: 1.0 ml/min

Detection: UV250 nm

<Result of Measurement>

HPLC surface purity: 93.4%

Further, as the result of measuring the NMR of the compound (f), the above structure was supported. The content of the obtained NMR is as follows.

δ=10.71 (s, 1H, phenol-OH), 8.73 (s, 1H, benzotriazole-H), 8.12 (d, 1H, J=9.6 Hz, benzotriazole-H), 7.98 (d, 1H, J=9.6 Hz, benzotriazole-H), 7.15 (m, 3H, phenol-H), 6.18 (s, 1H, C=CH$_2$—H), 5.62 (s, 1H, C=CH$_2$—H), 4.65 (m, 2H, methacryloyl-O—CH$_2$—H), 4.57 (m, 2H, benzotriazole-CO—O—CH$_2$—H), 3.89 (s, 3H, phenol-O—CH$_3$—H), 1.98 (s, 3H, CH$_2$=C—CH$_3$—H)

Comparative Example

As a comparative example, a compound (g); 3-(2H-benzotriazole-2-yl)-4-hydroxyphenethyl methacrylate that is a conventionally general ultraviolet light absorber was synthesized.

(Preparation of a Light Absorbing Film)

0.1 g of compound (e) obtained in Example 5, 1.9 g of polymethyl methacrylate, 4.0 g of methylethylketone, and 4.0 g of toluene were mixed and dissolved to obtain a solution of a resin composition having a light absorber. Then the obtained solution of the resin composition having a light absorber was applied onto a glass plate (2 mm thick) by using a bar coater No. 20, followed by heating and drying at 90° C. for 2 minutes, then followed by heating and drying at 120° C. for 3 minutes. After that, drying under reduced pressure was implemented at 40° C. for 12 hours to remove the solvent thereby obtaining a film of polymethyl methacrylate having 5% light absorber with the film thickness of 4 μm. In the meantime, the compounds (g) synthesized in Comparative Example was copolymerized with methyl methacrylate to prepare a copolymer that includes 5% light absorber, followed by filming them by the same method as in compound (e) thereby obtaining a film of polymethyl methacrylate having 5% light absorber with the film thickness of 4 μm.

[Light Blocking Test]

By placing the film of polymethyl methacrylate having 5% light absorber of the compounds (e) and (g) that were obtained in the above mentioned methods on transfer films of yellow dyes, cyan dyes, and magenta dyes, that are used for commercially available sublimation transfer type compact photo printer (Canon SELPHY CP600) to protect the transfer films, followed by irradiating simulated solar light for 100 hours by a weather meter to see color fading. Five criteria were set in which Level 5 signifies no fading, level 4 little fading, level 3 fading to some extent, level 2 much fading and level 1 complete fading. The results evaluated based on the above are shown in Table 1.

TABLE 1

| Light absorbing film | Compound (e) | Compound (g) (Comparison) | No film (Comparison) |
|---|---|---|---|
| Evaluation result of light blocking test | 5 | 3 | 2 |

From Table 1, it is found that compared with the conventional light absorber, the product related to the present invention has higher light blocking function for a long term, and therefore, it can be said that the product related to the present invention is a useful light absorber. For information, the condition of the light blocking test for the films in which the compound obtained from Examples and Comparative Example is as follows.

<Condition of Light Blocking Test>

Apparatus: Superxenon weather meter SX-75 (Suga Test Instruments Co., Ltd)

Irradiation intensity: 180 W/m$^2$

Irradiation time: 100 hours

Black panel temperature: 63° C.

Tank moisture: 50%

INDUSTRIAL AVAILABILITY

The benzotriazole derivative compound of the present invention exhibits a maximum absorption wavelength in a vicinity of 310 nm and 380 nm, with excellent ultraviolet light blocking function and excellent light blocking function for a visible light short wavelength range, and therefore, the light blocking function is not damaged even when exposed to solar light for a long time. Thus, it can be utilized for a material that deteriorates with ultraviolet light and the light of a visible light short wavelength range and for protection of a human body.

Figure 1:
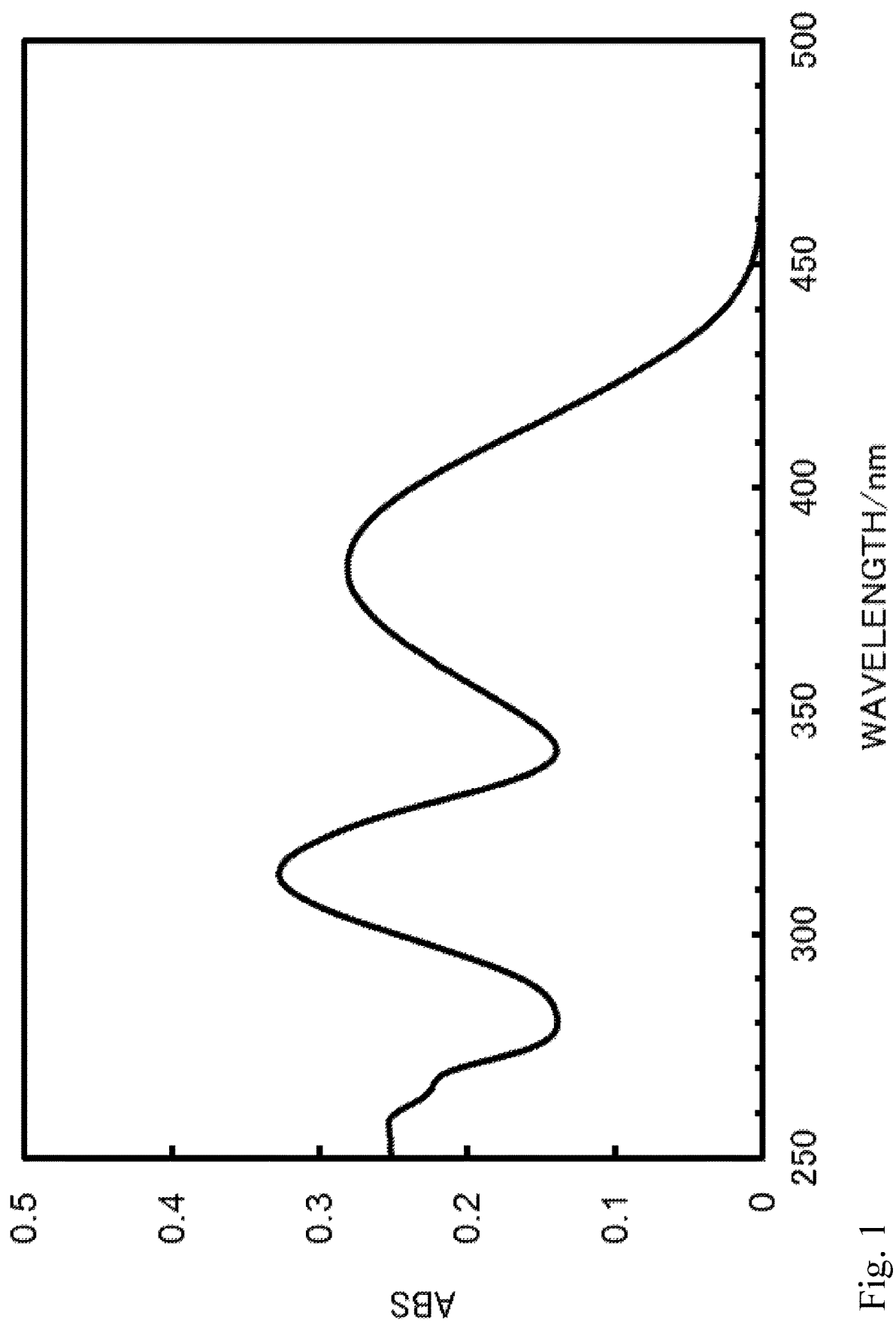
FIG. 1 shows UV-visible absorption spectrum of a compound (a).
Figure 2:
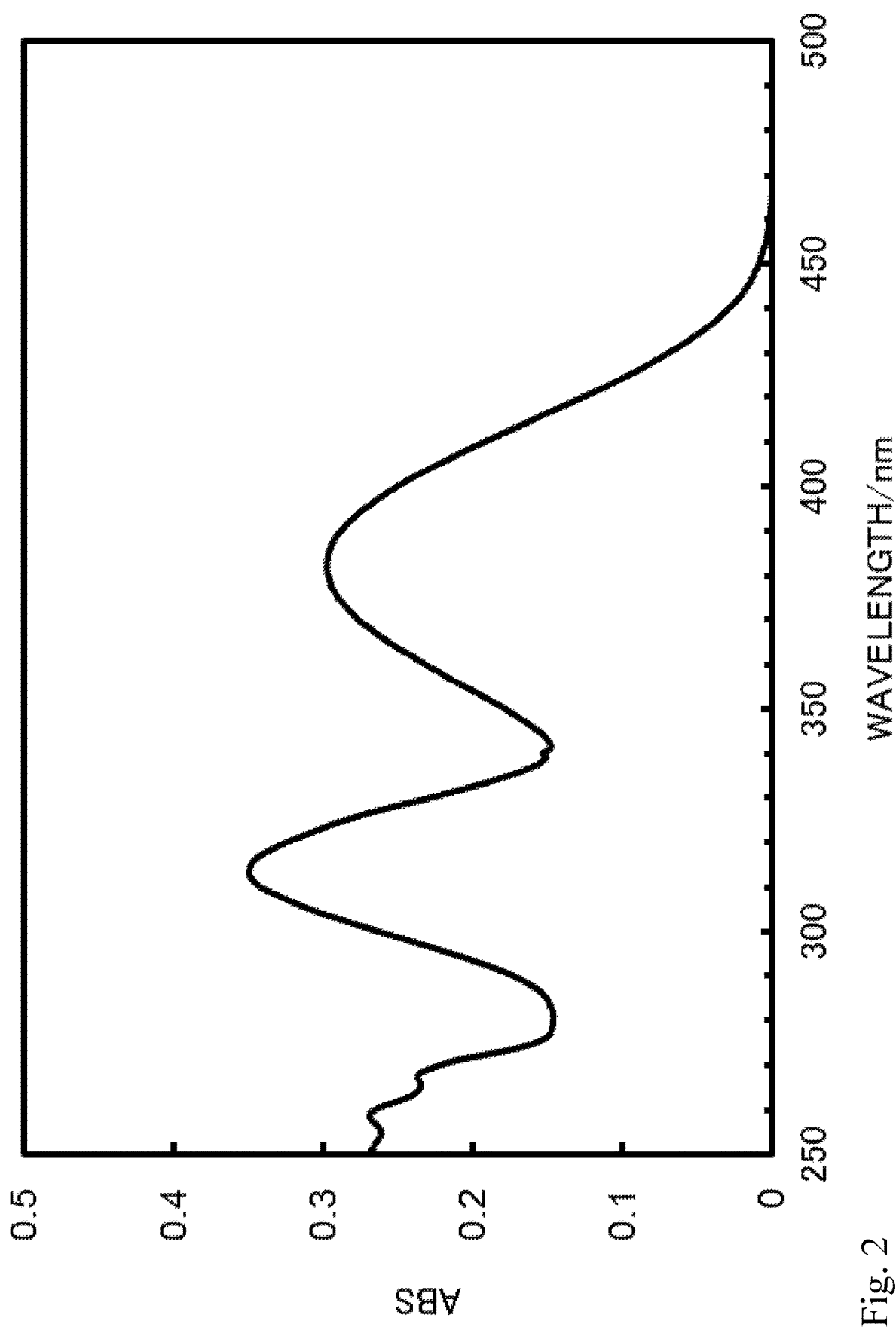
FIG. 2 shows UV-visible absorption spectrum of a compound (b).
Figure 3:
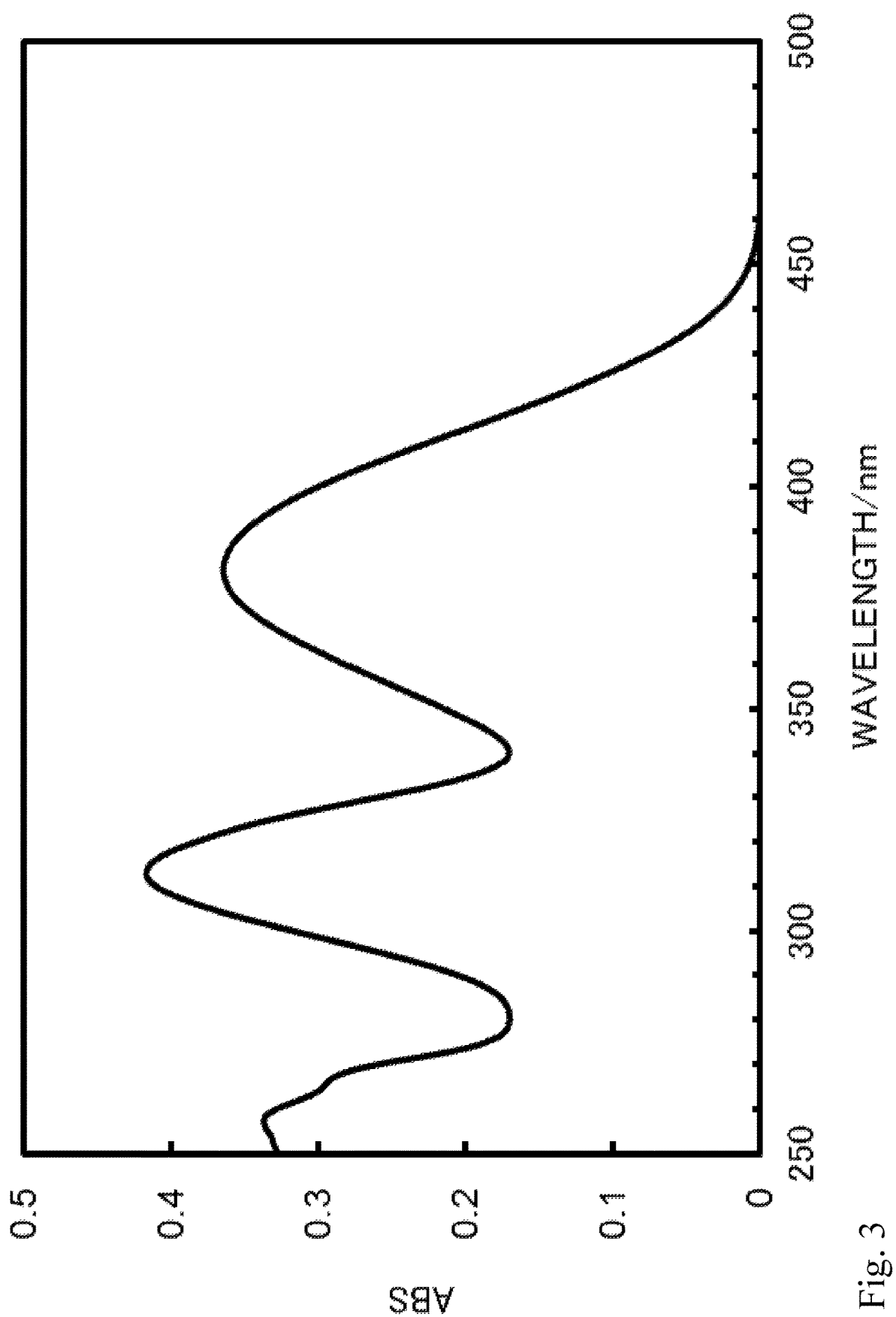
FIG. 3 shows UV-visible absorption spectrum of a compound (c).
Figure 4:
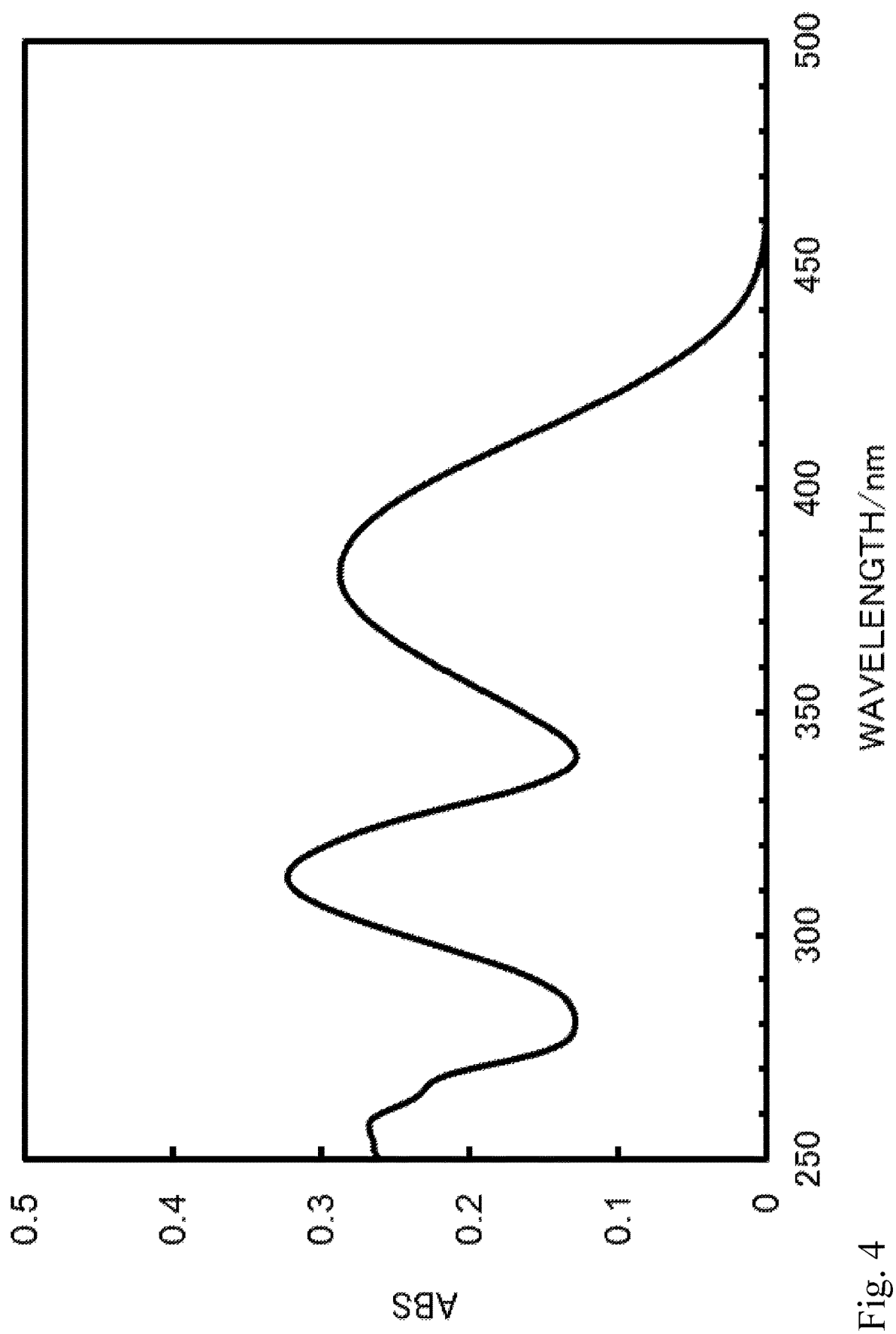
FIG. 4 shows UV-visible absorption spectrum of a compound (d).
Figure 5:
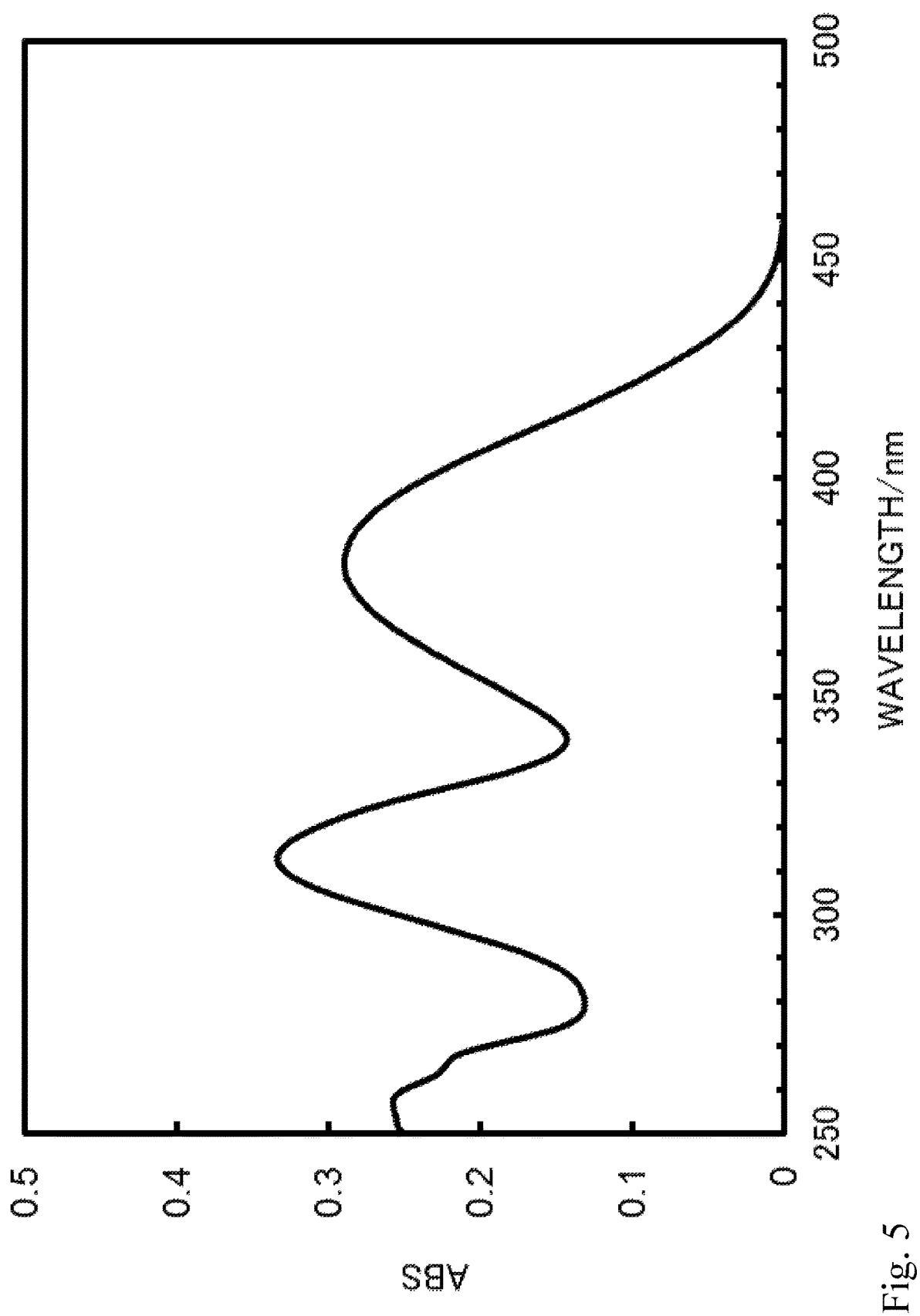
FIG. 5 shows UV-visible absorption spectrum of a compound (e).
Figure 6:
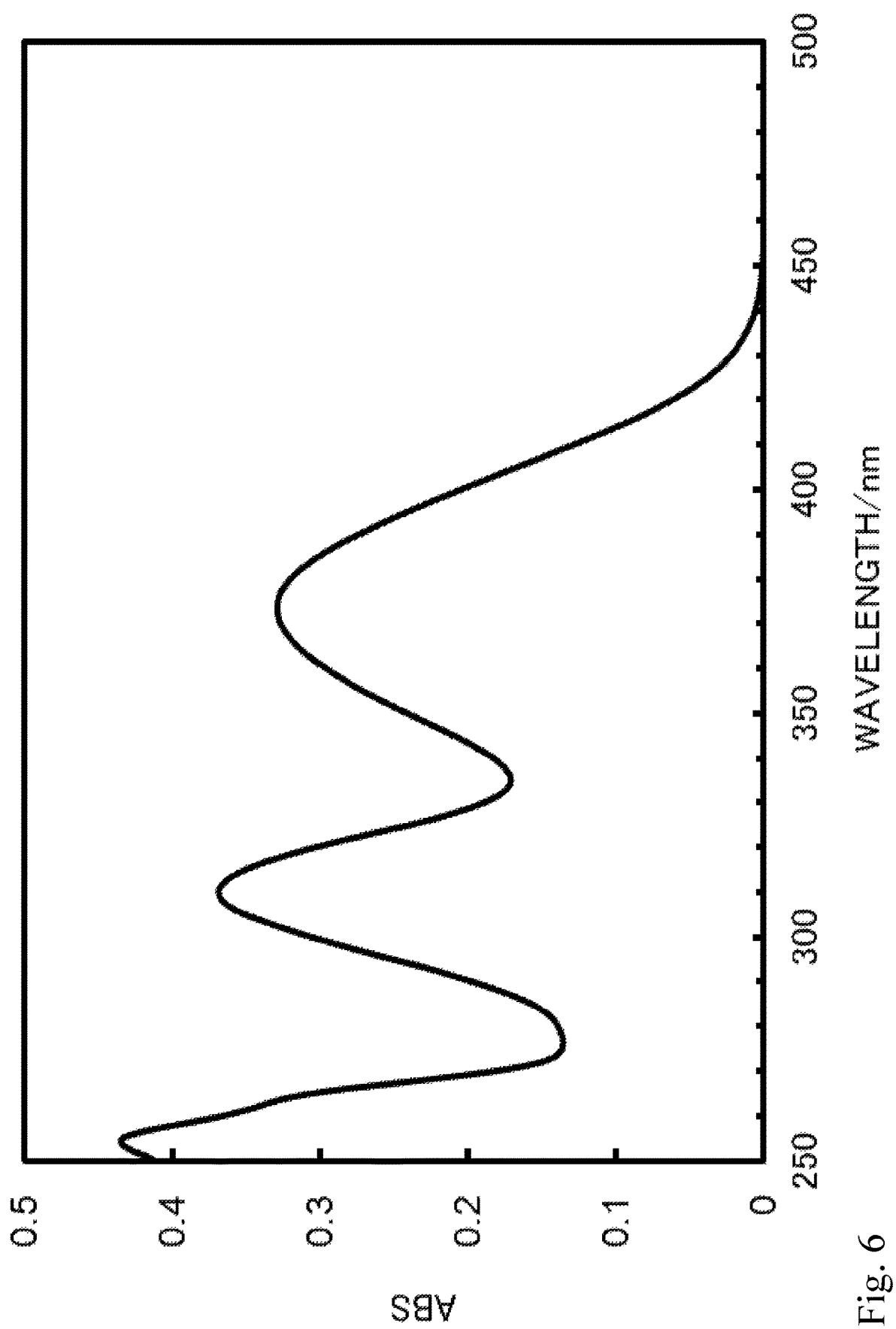
FIG. 6 shows UV-visible absorption spectrum of a compound (f).

The invention claimed is:

1. A benzotriazole derivative compound represented by the following general formula (1):

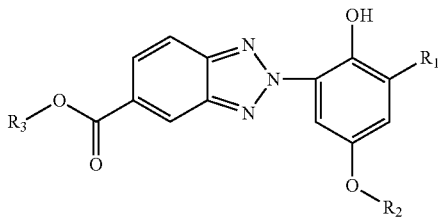

General formula (1)

wherein $R_1$ in the above general formula (1) is a hydrogen atom, or an alkyl group whose carbon number is 1 to 8, wherein $R_2$ in the above general formula (1) is an alkyl group whose carbon number is 1 to 8, and wherein $R_3$ in the above general formula (1) is an acryloyl oxyalkyl group whose alkyl carbon number is 1 to 2 or a methacryloyl oxyalkyl group whose alkyl carbon number is 1 to 2.

2. A light-absorber including the benzotriazole derivative compound according to claim 1.

3. A light-absorbing resin composition wherein the benzotriazole derivative compound according to claim 1 is compounded in a resin.

* * * * *